(12) United States Patent
Le et al.

(10) Patent No.: US 9,827,122 B2
(45) Date of Patent: Nov. 28, 2017

(54) SYSTEM FOR A CATHETER

(71) Applicant: Abbott Cardiovascular Systems Inc., Santa Clara, CA (US)

(72) Inventors: Tram U. Le, Corona, CA (US); Justin Mann, Lake Elsinore, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 227 days.

(21) Appl. No.: 14/703,697

(22) Filed: May 4, 2015

(65) Prior Publication Data

US 2016/0324669 A1    Nov. 10, 2016

(51) Int. Cl.
*A61F 11/00* (2006.01)
*A61F 2/95* (2013.01)
*A61F 2/966* (2013.01)
*A61M 25/00* (2006.01)

(52) U.S. Cl.
CPC ............... *A61F 2/95* (2013.01); *A61F 2/966* (2013.01); *A61M 25/0009* (2013.01); *A61M 25/0026* (2013.01); *A61F 2002/9517* (2013.01); *A61F 2240/002* (2013.01); *A61M 25/0021* (2013.01); *A61M 25/0023* (2013.01); *A61M 25/0045* (2013.01); *A61M 2025/0035* (2013.01); *A61M 2025/0037* (2013.01)

(58) Field of Classification Search
CPC .............. A61F 2/95; A61F 2002/9517; A61M 25/0021; A61M 25/0023; A61M 25/0026; A61M 25/0045; A61M 2025/0035
See application file for complete search history.

(56) References Cited

U.S. PATENT DOCUMENTS

| 4,775,371 | A | 10/1988 | Mueller et al. |
| 5,308,342 | A | 5/1994 | Sepetka et al. |
| 6,663,614 | B1 | 12/2003 | Carter |
| 8,725,228 | B2 | 5/2014 | Koblish et al. |

*Primary Examiner* — Robert Lynch
(74) *Attorney, Agent, or Firm* — David J. Pitman; Fulwider Patton LLP

(57) ABSTRACT

A system for providing a continuous passage through a delivery catheter comprising a handle that defines an internal chamber. A first tube having a proximal end and a distal end and a first bore, the first tube being fixedly mounted within the handle, wherein the first bore at the distal end of the first tube is shaped to define a first inverse conical surface. A second tube having a proximal end and a distal end and a second bore, the second tube being slidably mounted within the handle, wherein the second bore is in axial alignment with the first bore. A third tube having a proximal end and a distal end and a third bore.

14 Claims, 5 Drawing Sheets

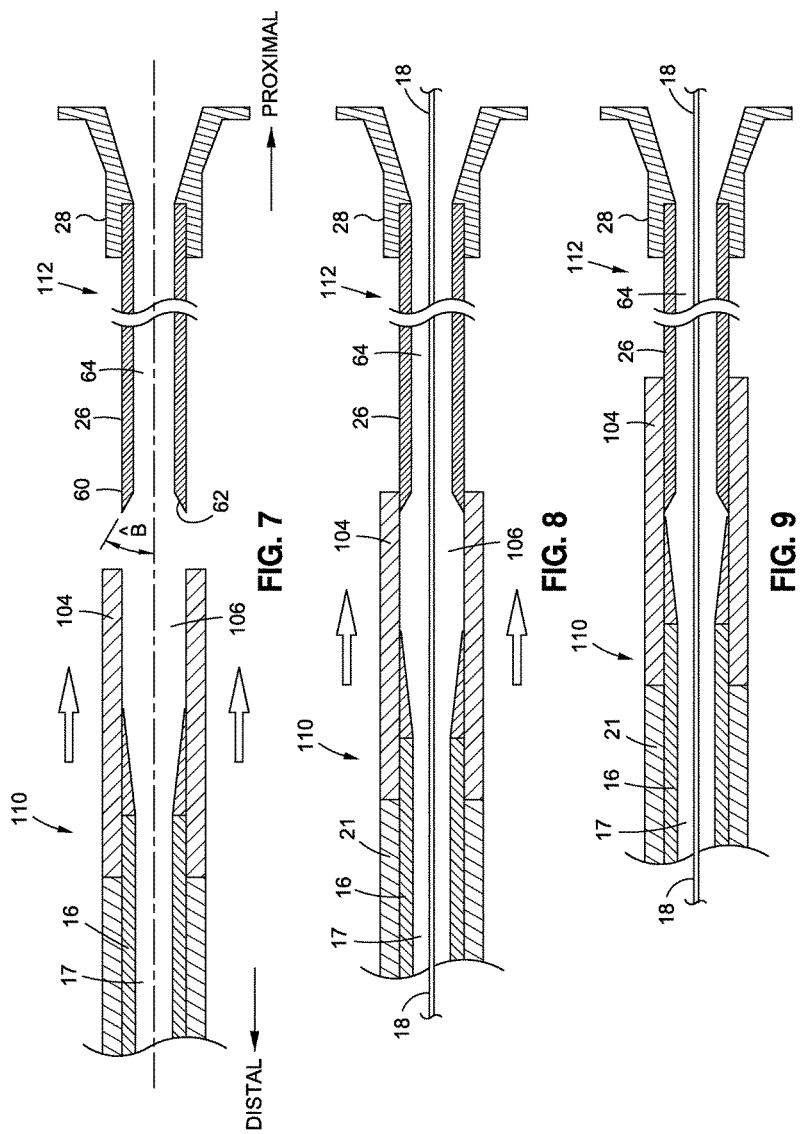

SYSTEM FOR A CATHETER

BACKGROUND

The present invention relates to a system for delivering a self-expanding stent to a body vessel that requires reinforcement in situations where the vessel may have become occluded, or where the vessel may have lost its structural strength and is tending to collapse. More specifically, the invention is related to the catheter technology set forth in application Ser. No. 13/118,325, published as U.S. 2011/0295354 and which is incorporated herein in its entirety. In prior art inventions such as the cited application, a catheter system may be provided that requires two tubes located in a catheter handle to be axially aligned with each other, and to be capable of moving axially in relation to each other. Further, one tube may be configured to slide axially within the handle of the catheter and, therefore, to move axially in relation to the other tube which may be fixed. This movable tube may be operably connected to a stent advancement member. The stent advancement member may be shaped to have forward pointing barbed elements, capable of engaging with a self-expanding stent in a compressed condition, and forcing the stent distally out of a sheath in a series of oscillating movements that include a series of distal movements.

Significantly, such axially aligned tubes may also be configured to receive a guidewire that extends axially down the bore of both tubes. It is frequently desirable that the distal end of the guidewire may be inserted into the tubes from the proximal end of the catheter, and also that the proximal end of the guidewire may be inserted into the tubes from the distal end of the catheter. Yet a problem arises in the prior art because the junction between the two axially aligned tubes typically presents a geometry in which the end of the guidewire, either the distal tip or the proximal end, may become snagged or blocked by engagement with one of the tube ends during insertion.

Accordingly, there is a need in the prior art for a system of axially aligned tubes, capable of axial movement in relation to each other, that may be conveniently and inexpensively installed in a catheter that addresses the needs in the prior art. The present invention addresses these and other needs.

SUMMARY OF THE INVENTION

The present invention, in one embodiment, is a system for providing a continuous passage through a delivery catheter. The system comprises a handle that defines an internal chamber. A first tube having a proximal end and a distal end and a first bore is provided, the first tube being fixedly mounted within the handle, wherein the first bore at the distal end of the first tube is shaped to define a first inverse conical surface. A second tube having a proximal end and a distal end and a second bore is provided, the second tube being slidably mounted within the handle, wherein the second bore is in axial alignment with the first bore. A third tube having a proximal end and a distal end and a third bore is provided, wherein the second tube is positioned so that the proximal end of the second tube extends into the third bore at the distal end of the third tube for a first length of the third bore, and wherein the third tube is fixedly attached to the second tube. Further, the distal end of the first tube extends into the third bore at the proximal end of the third tube for a second length of the third bore, and wherein the third tube is slidable over the first tube. Additionally, a fourth tube having a fourth bore is provided, the fourth tube being positioned within the third bore and butting against the proximal end of the second tube, the fourth bore being shaped to define a second inverse conical surface that extends from an inner surface of the third bore toward the proximal end of the second tube. In some embodiments, the handle includes a button slidably mounted on the handle, and the button is operably connected to the second tube. A block may be slidably mounted within the internal chamber of the handle, the block being connected to the second tube, and the button is connected to the block. In some embodiments, the third tube is positioned within the internal chamber. And in other embodiments, at least a portion of the third tube and a portion of the second tube is surrounded by a shrink wrap polymer. Preferably, the first tube is formed of metal, and the second tube includes a braided polymer material. In further embodiments, the fourth tube is formed of a polymer that is flexible and suitable for heat setting. In some embodiments, the first inverse conical surface forms an angle of between 20 degrees and 40 degrees to an axis of the first inverse conical surface. And in yet further embodiments, the second inverse conical surface forms an angle of between 5 degrees and 30 degrees to an axis of the second inverse conical surface.

In another embodiment, the invention is a method for manufacturing a continuous passage having a length through a delivery catheter, wherein the length of the continuous passage is configured to be increased and decreased sequentially. The method comprises forming a first assembly by: positioning a polymer tube on a tapered portion of a mandrel having a conically tapered portion and a cylindrical portion; positioning a first shaft that is hollow onto the tapered portion of the mandrel so that the first shaft abuts the polymer tube; positioning a second shaft that is hollow on the cylindrical portion of the mandrel so that the second shaft overlaps with a portion of the first shaft; positioning a shrink tube over at least a portion of the first shaft and a portion of the second hollow shaft; heating the polymer tube, the first tube the second tube and the shrink tube and the mandrel to form a bond between the first tube and the second tube and to impart an inverse conical surface to an internal bore of the polymer tube; removing the mandrel from the second shaft, whereby the polymer tube, the first shaft, the second shaft, and the shrink wrap tube are comprised in the first assembly. Additionally, forming a second assembly by: providing a fixed shaft that is hollow and having a distal end, a proximal end, and a bore; forming an inverse conical surface on the bore at the distal end; and installing at least a portion of the second assembly into a handle of a delivery catheter such that the second assembly is fixed in relation to the handle; installing at least a portion of the first assembly in the handle of the delivery catheter such that the second shaft slidably overlaps with the distal end of the fixed shaft, and the first assembly is slidable in relation to the handle. In some embodiments, the step of positioning a polymer tube on a tapered portion of a mandrel includes positioning an extruded polymer tube on a tapered portion of a mandrel. In other embodiments, the method further includes connecting the first assembly to a button slidably attached to an external surface of the handle of the delivery catheter.

These and other advantages of the invention will become apparent when considered in light of the drawings and the detailed description of some embodiments.

BRIEF DESCRIPTION OF THE DRAWINGS

FIG. 7 is a schematic sectional view of components of a catheter, having features of an embodiment of the invention, shown in a first condition.

FIG. 8 is a schematic sectional view of the components shown in FIG. 7, shown in a second condition.

FIG. 9 is a schematic sectional view of the components shown in FIG. 7, shown in a third condition.

DETAILED DESCRIPTION OF THE SOME EMBODIMENTS

Figure 1:
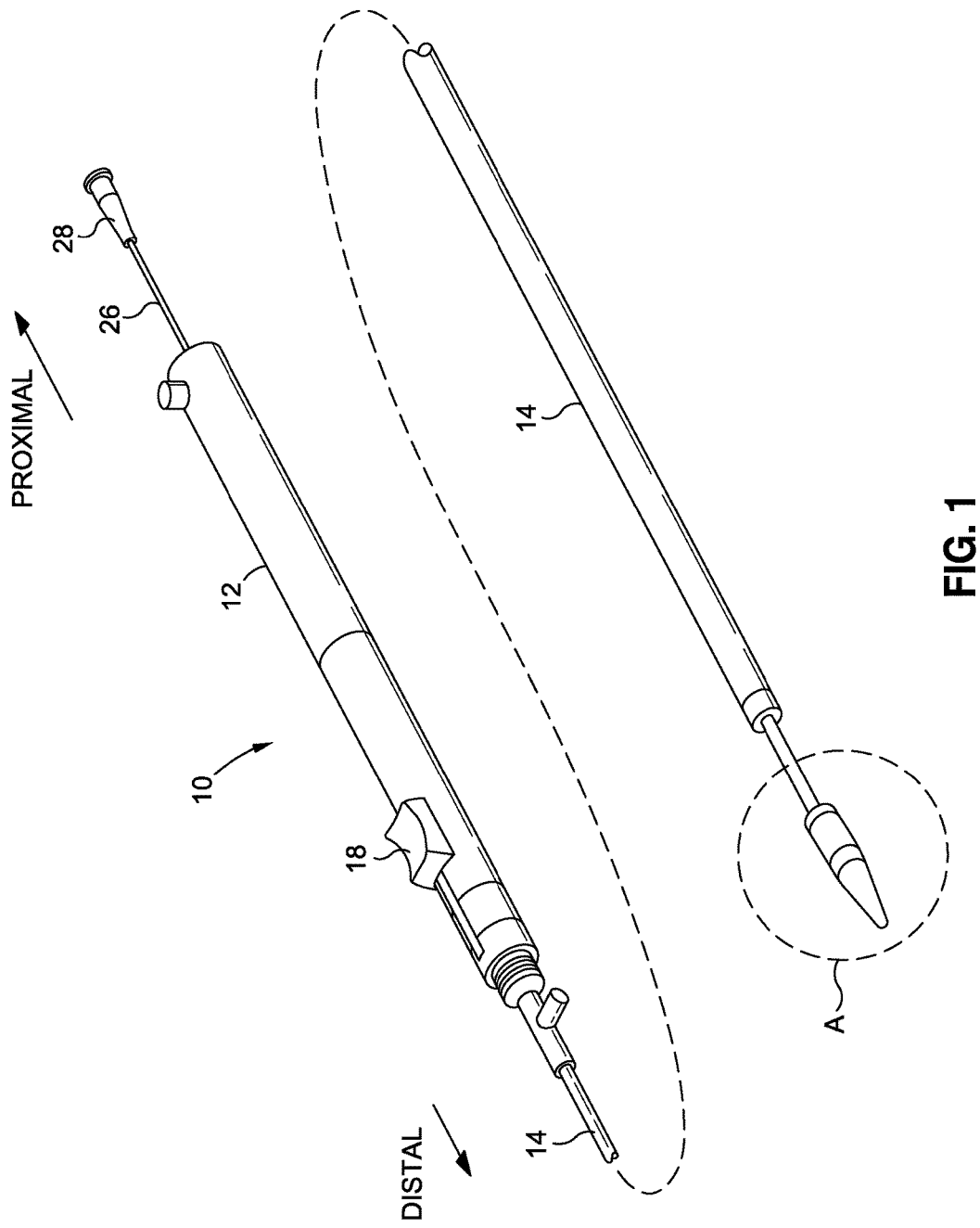
FIG. 1 is a schematic perspective view of a catheter suitable for including features of the present invention.

The present invention is described with reference to the figures, which exemplify embodiments of the invention. With reference to FIG. 1, a catheter 10 having a handle 12 is shown. Extending distally from the handle is an outer cover 14 or sheath which is configured to enclose a self-expanding stent 30 (seen in FIG. 2) in a collapsed condition. The sheath 14 is sized to be inserted into the vasculature of a patient, and the stent is configured to expand to an expanded condition, as schematically exemplified in FIG. 2, when it is released from the confines of the sheath 14 by being advanced distally out of the distal end of the sheath. The catheter of FIG. 1 may, optionally, also include additional structure to facilitate placement of the sheath within the patient's vasculature, and also to facilitate protection of the stent during delivery (as may be identified in detail A in FIG. 1), but this optional detail to catheters of the general kind is not further described herein.

A primary purpose of the handle 12 is to allow a surgeon user to control the sheath 14 as the sheath is inserted into the patient's vasculature; and then, once the sheath is in desired position, to allow the surgeon to repeatedly push the stent 30 distally until it emerges entirely from its collapsed condition within the sheath 14.

In order to accomplish its intended result, the catheter 10 is provided with a number of structural features. The handle 12 may be formed from a plurality of molded polymer components 12a, 12b, 12c, according to known technology, as shown in FIG. 2, in order to facilitate assembly of the handle.

Figure 2:
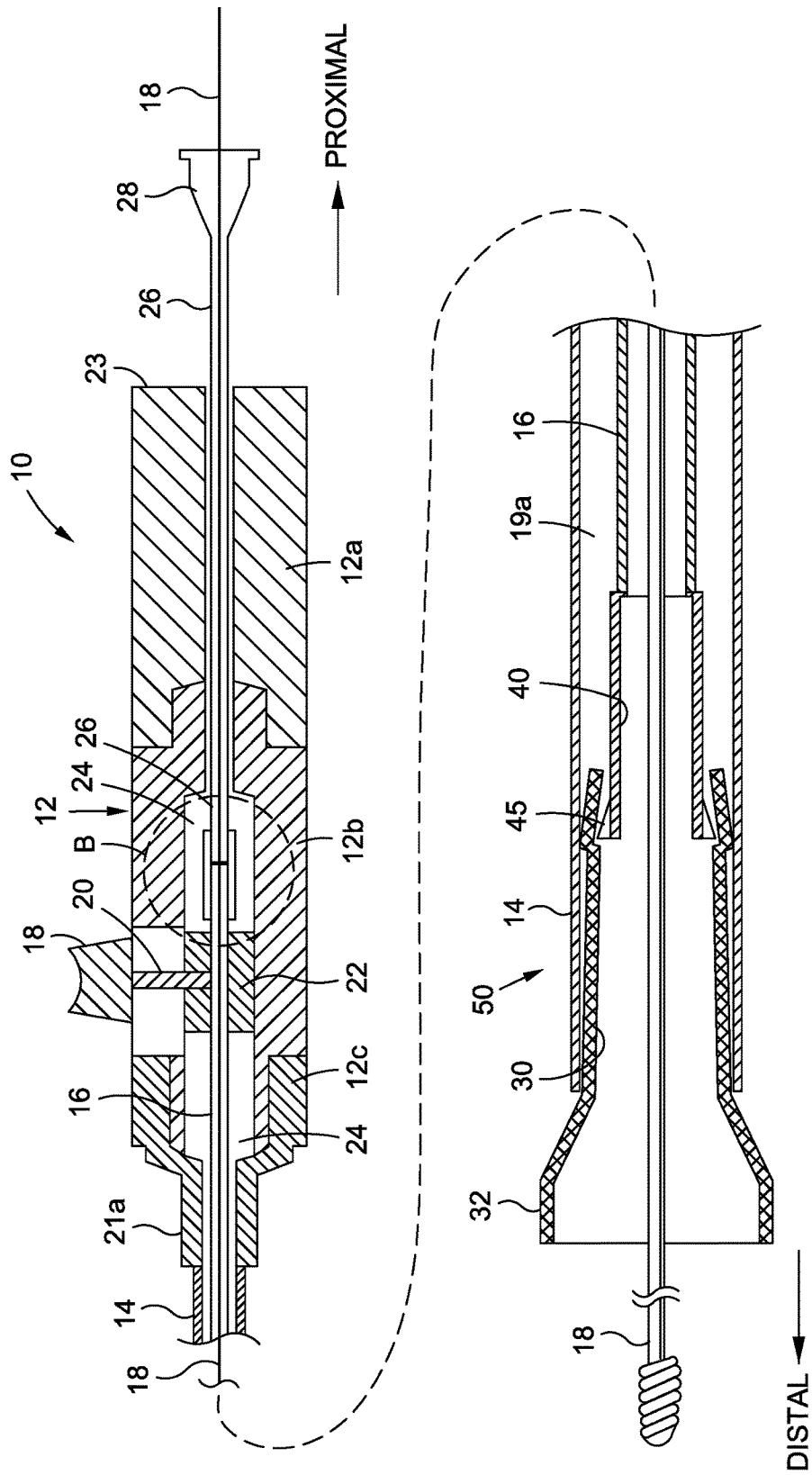
FIG. 2 is a schematic sectional view of an embodiment of the catheter shown in FIG. 1, the sectional view showing features of an embodiment of the invention.

Turning to the distal tip 50 of the sheath, FIG. 2 shows how a stent 30 may be initially confined within the sheath 14 in a collapsed condition, and may be forced distally out from the confines of the sheath where the distal tip 32 of the stent assumes an expanded condition sufficiently large to contact the internal wall of a vessel lumen (lumen not shown in the figures).

In order to accomplish the distal movement of the stent 30 from the sheath 14, a stent deployment member 45 may be provided and operably connected to the distal end of a stent actuator 16. The stent actuator 16 may take the form of a hollow shaft that extends from the distal end of the catheter, within a bore of the sheath, to terminate within the handle 12. The stent actuator 16 may be hollow in order to allow a guidewire 18 to be passed along its length, in addition to flushing fluid and other structures where necessary. In some embodiments, the stent actuator 16 may be a shaft made of composite materials.

As seen in FIG. 2, the deployment member 45 is provided with distal sloping barbs configured to engage the wire mesh fabric of the stent 30. The barbs may be mounted on elastic arms 40 which are configured to provide a radially outward bias to the stent engagement member 45 so that the engagement member 45 is compelled to engage the stent 30 during a distal movement, but may be forced radially inwardly and out of engagement with the stent during a proximal movement due to the slope of the barb and the elasticity of the arms 40. The elastic arms 40 may be connected to the stent actuator 16 as seen (schematically) in FIG. 2. It will be appreciated that a series of oscillating sequential distal and proximal movements of the stent actuator 16 will result in the stent 30 being forced out of the distal end of the sheath 14 in a number of short sequential movements.

In order to impart such an oscillating distal and proximal motion to the stent actuator 16, the stent actuator may be configured to slidingly pass along the central bore 19a of the sheath 14 into the distal end 21a of the handle 12. The handle may be provided with a button 18 which is mounted to slide distally and proximally in relation to the handle. The button may be connected via a pin 20 to a block 22 installed to slide distally and proximally within a chamber 24 inside the handle 12. The stent actuator 16 passes through the block 22, and his fixedly held by the block so that relative movement between block and stent actuator is prevented. It will be appreciated that movement of the button 18 by the user's thumb will result in equivalent movement of the stent actuator 16 within the handle and, consequently also, by the stent deployment member 45 at the distal end of the sheath due to the operable connection between stent actuator 16 and stent deployment member 45.

The stent actuator 16 does not extend through to the proximal end 23 of the handle 12. Rather, the stent actuator 16 terminates in the center of the handle, and engages (as more fully described below) with a hollow fixed shaft 26 (preferably a hypotube made of metal) that is inserted and fixed into the proximal end 23 of the handle 12 so that it cannot slide in relation to the handle. The fixed shaft 26 terminates at its distal end at a location adjacent the proximal end of the stent actuator 16 and is co-axially aligned with the stent actuator, as will be described more fully below. At the proximal end of the fixed shaft 26, a female luer connector 28 may be fixed in order to permit connection to the usual surgical requirements such as flushing fluid, and to permit a guidewire 18 to be passed distally through the bore of the fixed shaft 26 and thence along the bore of the stent actuator 16 until the guidewire extends beyond the distal tip of the sheath. FIG. 2.

In one embodiment, the invention provides a novel and advantageous system for providing a continuous bore that runs from the bore 64 of the fixed shaft 26 into the bore 17 of the stent actuator 16 (FIG. 7), yet which allows that such continuous bore may be sequentially lengthened and shortened as the stent actuator 16 oscillates back and forth under the operation of the button 18 by the physician user. The location of the novel connection between these structures is identified at detail B in FIG. 2, within the chamber 24 of the handle 12. Details of certain embodiments are set forth hereunder.

The structural components included in detail B in FIG. 2 and the method of manufacture thereof is now described with reference to FIGS. 3-9. In one embodiment, the formation of the novel connection is commenced by manufacturing a first assembly 110 (FIGS. 7-9) that includes the stent actuator 16 according to the following procedure.

Figure 3:
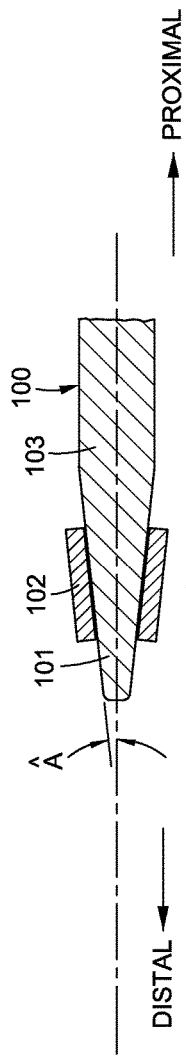
FIGS. 3-6 are sectional views taken through structures at various stages of manufacture of a component of the invention.

A short length of flexible tubing 102 is loaded onto a tapered mandrel 100, as seen in FIG. 3, the mandrel having a conical portion 101 and a cylindrical portion 103. Preferably, the flexible tubing is of a single-layered extrusion polymer. The flexible tubing 102 is positioned on the tapered or conical portion of the mandrel to leave a suitable length (between 5 mm and 20 mm) of the conical portion of the mandrel extending distally, not covered by the tubing.

Figure 4:
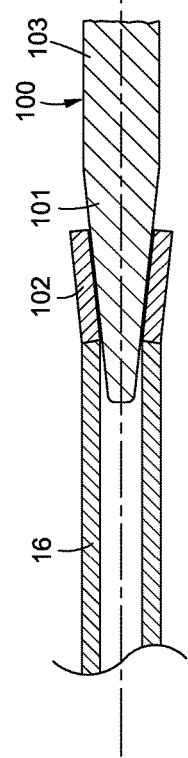

A hollow first shaft 16, which is configured to take on the role of the stent actuator 16, is loaded onto the small end of the cone 101 of the tapered mandrel 100, as seen in FIG. 4. The first shaft 16 is preferably of composite form. The first shaft 16 (also referred to herein as the stent actuator because it assumes the function of the stent actuator) is positioned adjacent the flexible tubing 102. As may be understood with reference to FIGS. 4-5, the outer diameter of the first shaft 16 (stent actuator) is selected to be substantially the same as the outer diameter of the cylindrical portion 103 of the mandrel 100.

Figure 11:
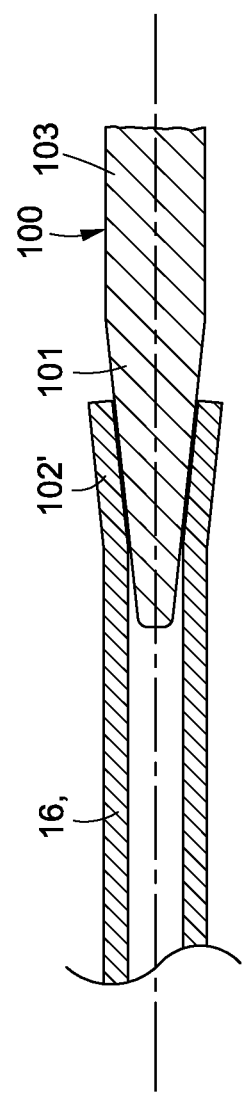
FIG. 11 is an alternative embodiment of the structures seen in FIG. 4.

FIG. 11 shows an alternative embodiment to FIG. 4, but follows the same principle as exemplified in FIG. 4. In this embodiment, the flexible tubing 102 of FIG. 4 is replaced with a modified flexible tubing 102', which may be a continuation of a modified first shaft 16', as seen in FIG. 11. Thus, in this embodiment, modified flexible tubing 102' and modified first shaft 16' form a unitary structure. In some embodiments, the modified flexible tubing may be formed of an outer layer of the modified first shaft 16', to give the modified flexible tubing 16' a desired degree of flexibility, while an inner layer of the modified first shaft may impart a required rigidity. The method of manufacture as described herein follows the same steps hereafter for both embodiments.

Figure 5:
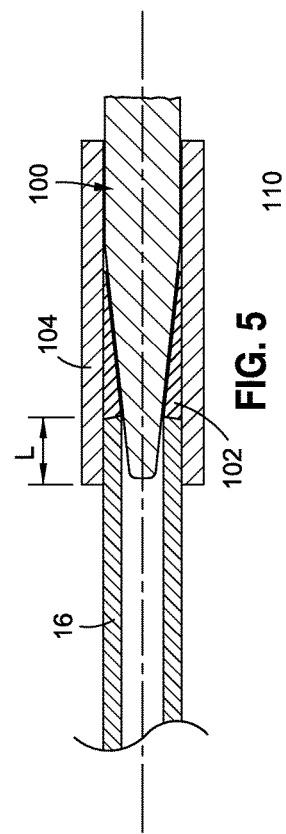

A short length of a hollow second shaft 104 is loaded onto the cylindrical end 103 of the tapered mandrel 100, so that a convenient length "L" (FIG. 5), between 5 mm and 30 mm, of the second shaft 104 overlaps with the first shaft 16, as seen in FIG. 5. (The second tube 104 may be loaded from either the proximal end or the distal end of the mandrel 100.) The inner diameter of the second shaft 104 is selected to snugly fit over the cylindrical portion of the mandrel 100. It will be appreciated that this selection will also cause the second shaft 104 to snugly fit over the outside diameter of the first shaft 16 as seen in FIG. 5.

Figure 6:
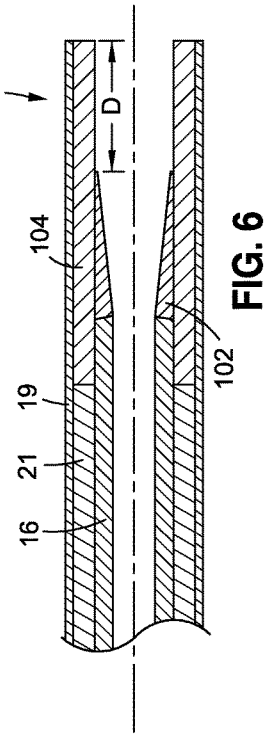

A covering shaft 21 may optionally be installed over the first shaft 16 as reinforcing. Once this step is complete, a shrink tubing 19 (see FIG. 6) may be loaded over the resulting assembly 110, and heat may be applied to create a bond between the external elements of the assembly. The heat will also cause the flexible tubing 102 to assume, as a permanent shape, the shape that it is forced to assume when sandwiched between the first shaft 16 and second shaft 104 and the mandrel 100. Thus, the angle "A" (FIG. 3) between the exterior surface of the cone 101 and the axis of the mandrel will be imparted to the internal surface of the bore of the flexible tubing 102, and this angle is preferably selected to be between 5 degrees and 30 degrees to the elongate axis of the mandrel. (As used herein, the term "inverse conical surface" will be used to describe the shape of an internal surface of a bore of an object that is formed by being molded onto an outside surface of a cone, or which could be placed in contact with an outside surface of a cone. This term will be applied even where the inverted conical surface is truncated, such as may arise from molding on a frusto-conical shape. Thus, as described, the internal surface of the flexible tubing 102 has the shape of an inverse conical surface.) When these steps are completed, the mandrel is removed from the assembly to leave the first and second shafts 16, 104 connected to each other, as shown in FIG. 6. The flexible tubing 102 forms a transition zone in the bore 106 of the combined assembly 110 in which the inner diameter of the second shaft 104 is gradually reduced to the inner diameter of the first shaft 16 (stent actuator) so that internal obstructions to a guidewire inserted into the bore 106 are avoided.

The fixed shaft 26 is also prepared prior to being fixedly inserted into the handle 12. With reference to FIG. 7, such preparation includes creating an internal slope or chamfer 62 on the internal bore 64 of the fixed shaft 26 at its distal end 60. The chamfer may be created by turning a conically shaped drill bit that is inserted into the distal end 60 of the bore 64. The slope of the chamfer as reflected by angle "B" (FIG. 7) is preferably set between 20 degrees and 40 degrees to the longitudinal axis of the fixed shaft. The fixed shaft 26 is also selected so that its external diameter will snugly fit into the inner diameter of the second shaft 104, as may be envisaged with reference to FIGS. 7-9. The fixed shaft and its related features will be referred to herein as the second assembly 112.

Figure 10:
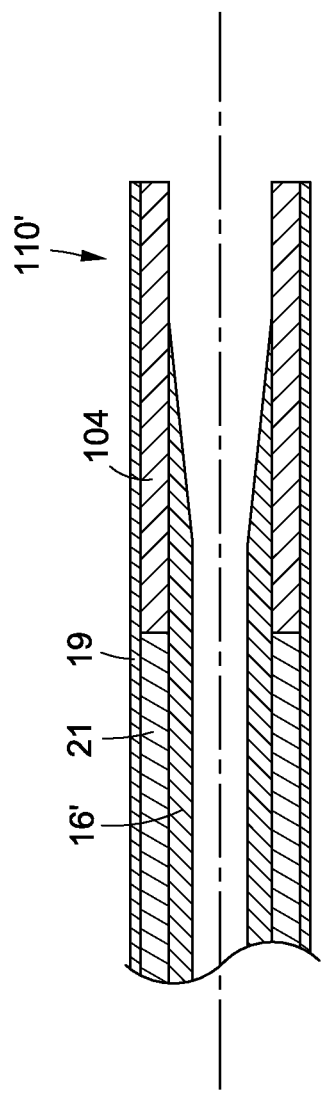
FIG. 10 is a schematic view of another embodiment of a component of the invention.

With reference to FIG. 10, a further embodiment 110' of the first assembly may be achieved by eliminating the flexible tubing 102, and by drilling the internal bore of the first shaft 16 from the proximal end with a conically shaped drill bit. The same geometric configuration for the internal surfaces of the combined bore as those seen in FIG. 6 are preferred.

Once the first assembly 110 and the second assembly 112 are prepared according to the foregoing description, the handle 12 of the catheter is assembled. The second assembly 112 is installed into the handle so that it is fixed in relation to the handle 12. Further, the first assembly 110 is brought up to the distal end 60 of the fixed shaft 26, as schematically shown in FIG. 7. (Handle not shown in FIGS. 7-9 for clarity.) The proximal end of the second shaft 104 is slipped over the distal end of the fixed shaft 26 as shown in FIG. 8, so that the second shaft is capable of sliding proximally over the fixed shaft. Once the first assembly 110 reaches the end of its proximal travel (as seen in FIG. 9) it is free to slide distally back to its starting position as in FIG. 8.

The net result is schematically shown in FIG. 2, where the first shaft 16 (stent actuator) and fixed shaft 26 are aligned with each other, the fixed shaft remains stationary in relation to the handle 12, and the stent actuator 16 is configured to be movable in an oscillating motion distally and proximally under the action of the button 18 by the physician user.

A first advantage of the described configuration is that the first shaft bore 17 and the fixed shaft bore 64 remain in alignment with each other during the oscillating motion of the first shaft 16 (stent actuator) for smooth operation of the catheter.

A further advantage provided by the resulting structure is that a guidewire 18 may be inserted down the combined bores 17, 64 of the first assembly and second assembly, (as seen in FIGS. 8 and 9)—either proximally from the distal tip 50 of the catheter, or distally from the luer connector 28 on the fixed shaft—without encountering any sharp internal obstructions at the point of connection between the first assembly 110 and the second assembly 112. This advantage remains in place no matter what the state of displacement of the first shaft 16 (stent actuator) in relation to the fixed shaft 26. This advantage may be appreciated by reference to FIGS. 8 and 9 that show the advantageous features of the resulting connection remain present throughout movement of the stent actuator 16. Accordingly, if a physician inserts a guidewire from either end of the catheter, then, no matter how much movement may have been imparted to the stent actuator 16 between FIG. 8 and FIG. 9, the advantageous features remain present in the overall assembly.

By way of clarification of terms that appear in some of the claims, the following elements that have been described above may also be referred to by different reference names, as follows. The fixed shaft 26 may be referred to as a first tube. The first shaft 16 may be referred to as a second tube. The second shaft 104 may be referred to as a third tube. The flexible tubing 102 may be referred to as a fourth tube.

Although preferred illustrative variations of the present invention are described above, it will be apparent to those skilled in the art that various changes and modifications may be made thereto without departing from the invention. For example, it will be appreciated that combinations of the features of different embodiments may be combined to form another embodiment. It is intended in the appended claims to cover all such changes and modifications that fall within the true spirit and scope of the invention.

We claim:

1. A system for providing a continuous passage through a delivery catheter, the system comprising:
    a handle that defines an internal chamber;
    a first tube having a proximal end and a distal end and a first bore, the first tube being fixedly mounted within the handle, wherein the first bore at the distal end of the first tube is shaped to define a first inverse conical surface;
    a second tube having a proximal end and a distal end and a second bore, the second tube being slidably mounted within the handle, wherein the second bore is in axial alignment with the first bore;
    a third tube having a proximal end and a distal end and a third bore,
        wherein the second tube is positioned so that the proximal end of the second tube extends into the third bore at the distal end of the third tube for a first length of the third bore, and wherein the third tube is fixedly attached to the second tube;
        wherein the distal end of the first tube extends into the third bore at the proximal end of the third tube for a second length of the third bore, and wherein the third tube is slidable over the first tube; and
    a fourth tube having a fourth bore, the fourth tube being positioned within the third bore and butting against the proximal end of the second tube, the fourth bore being shaped to define a second inverse conical surface that extends from an inner surface of the third bore toward the proximal end of the second tube.

2. The system of claim 1, wherein the handle includes a button slidably mounted on the handle, and the button is operably connected to the second tube.

3. The system of claim 2, wherein a block is slidably mounted within the internal chamber of the handle, the block is connected to the second tube, and the button is connected to the block.

4. The system of claim 2, wherein the third tube is positioned within the internal chamber.

5. The system of claim 1, wherein at least a portion of the third tube and a portion of the second tube is surrounded by a shrink wrap polymer.

6. The system of claim 1, wherein the first tube is formed of metal.

7. The system of claim 1, wherein the second tube includes a braided polymer material.

8. The system of claim 1, wherein the fourth tube is formed of a polymer.

9. The system of claim 1, wherein the first inverse conical surface forms an angle of between 20 degrees and 40 degrees to an axis of the first inverse conical surface.

10. The system of claim 1, wherein the second inverse conical surface forms an angle of between 5 degrees and 30 degrees to an axis of the second inverse conical surface.

11. The system of claim 1, wherein the second tube and the fourth tube are integrally formed.

12. A system for providing a continuous passage through a delivery catheter, the system comprising:
    a handle that defines an internal chamber;
    a fixed shaft having a proximal end and a distal end and a first bore, the fixed shaft being fixedly mounted within the handle, wherein the first bore at the distal end of the fixed shaft is shaped to define a first inverse conical surface;
    a first shaft having a proximal end and a distal end and a second bore, the first shaft being slidably mounted within the handle, wherein the second bore is in axial alignment with the first bore, and wherein the second bore at the proximal end of the first hollow shaft is shaped to define a second inverse conical surface;
    a second shaft having a proximal end and a distal end and a third bore,
        wherein the first shaft is positioned so that the proximal end of the first shaft extends into the third bore at the distal end of the second shaft for a first length of the third bore, and wherein the second shaft is fixedly attached to the first shaft; and
        wherein the distal end of the fixed shaft extends into the third bore at the proximal end of the second shaft for a second length of the third bore, and wherein the second shaft is slidable over the fixed shaft.

13. The system of claim 12 wherein the first inverse conical surface forms an angle of between 20 degrees and 40 degrees to an axis of the first inverse conical surface.

14. The system of claim 12, wherein the second inverse conical surface forms an angle of between 5 degrees and 30 degrees to an axis of the second inverse conical surface.

* * * * *